(12) United States Patent
Shanbrom

(10) Patent No.: US 6,841,060 B2
(45) Date of Patent: *Jan. 11, 2005

(54) METHOD FOR QUANTIFYING ANTIOXIDANT LEVELS IN FOOD AND MEDICAL SPECIMENS

(75) Inventor: Edward Shanbrom, Santa Ana, CA (US)

(73) Assignee: Shanbrom Technologies, LLC, Ojai, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/315,688

(22) Filed: May 20, 1999

(65) Prior Publication Data

US 2002/0117403 A1 Aug. 29, 2002

(51) Int. Cl.$^7$ ............................................. G01N 27/333
(52) U.S. Cl. .................... 205/775; 205/778.5; 205/779; 205/787; 205/792; 436/904
(58) Field of Search .............................. 205/775, 778.5, 205/779, 793.5, 792, 787; 436/124, 125, 128, 129, 131, 149, 904

(56) References Cited

U.S. PATENT DOCUMENTS

| | | | |
|---|---|---|---|
| 4,141,688 A | | 2/1979 | Morris et al. |
| 4,300,905 A | | 11/1981 | Bleisteiner et al. |
| 6,108,570 A | * | 8/2000 | Kohen et al. ............... 600/345 |

OTHER PUBLICATIONS

Alexander, "Reaction of povidone–iodine with amino acids and other important biological compounds", Proc. Int. Symp. Povidone, pp. 274–288, Apr. 1983.*

Coetzee, "Polyvinylpyrrolidone–iodine solutions as oxidizing agents in titrimetric determinations"S. Afr. J. Chem. 44, pp. 22–24, Mar. 1991.*

Cheregi et al, "Flow Injection Determination of L–Ascorbic Acid in Natural Juice with Biamperometric Detection", Anal. Lett. 30 (14), pp. 2625–2640, Apr. 1983.*

Chen "Determination of ascorbic acid in drinks using cyanide–selective electrode with the addition of iodine", Huaxue Chuanganqi, 15, pp. 295–297 (inlcuding CAS abstract), month N/A 1995.*

Motonaka et al, "Differential determination of a mixture of vitamin A and beta–carotene by potentiometric titration utilizing N–bromosuccinimide and iodine", Bunseki Kagaku, 44, pp. 1013–1019 (including CAS abstract), Month N/A 1983.*

Karlsson, "Iodometric Determination of Ascorbic Acid by Controlled Potential Coulometry", Talanta 22, pp. 989–993, Dec. 1995.*

Nicholas et al, "Antioxidants and Antiozonants", Kirk–Othmer Encyclopedia of Chemical Technology, 3rd Ed., pp. 128–148, Month N/A 1978.*

Hampel et al, "Antioxidant", Glossary of Chemical Terms, 2nd Ed., month N/A 1992.*

Translation of Chen, Chemical Sensors, vol. 15, pp. 295–297, Dec. 1995.*

Solinas et al, Ind. Agr. (Florence) (1968), 6, pp. 21–24 (CAS Abstract only).*

Christova et al., Anal. Chim. Acta, 1976, 85, pp. 301–307.*

Amiel M. Farrington et al., "Simple Solid Wire Microdisc Electrodes for the Determination of Vitamin C in Fruit Juices", Feb. 1994, pp. 233–238.

Andrei Danet, et al., "Dispozitiv de analiza in flux cu injectare hidrodinamica", 1994, pp. 1000 (English abstract included).

Search Report, Issued May 20, 1999 for International Application No. PCT/US 00/11899.

* cited by examiner

*Primary Examiner*—Kaj K. Olsen
(74) *Attorney, Agent, or Firm*—Reed Smith LLC

(57) ABSTRACT

A simple analytical method for determining antioxidant level in food product and body fluids such as urine is based on reduction of elemental iodine. The method adds an aqueous solution of iodine and an iodophor to the sample to be tested. Polyvinylpyrrolidone is a preferred iodophor. Antioxidant materials in the sample reduce the elemental iodine and the reaction is monitored by measuring either a decrease in iodine or an increase in iodide ion. A preferred method of practicing the invention is to measure the change in iodide ion with an ion selective electrode and an appropriate electronic meter. The method rapidly and inexpensively produces antioxidant measurements that are comparable to those produced by my more complex and cumbersome methods.

6 Claims, No Drawings

METHOD FOR QUANTIFYING ANTIOXIDANT LEVELS IN FOOD AND MEDICAL SPECIMENS

BACKGROUND OF THE INVENTION

1. Field of the Invention

The present application concerns biology and biological chemistry and more particularly measurement of antioxidant properties of foods and biological specimens.

2. Description of Related Art

Recently there has been a revolution in human nutrition and our understanding of the relationship between human health and diet. Most of us take for granted that foods contain vitamins and that these compounds are responsible for many of the beneficial properties of food. However, this belief is a recent one. The first vitamin to be scientifically identified and described was vitamin A (retinol) which was not described until 1913. The most recently identified of the "core" vitamins is vitamin $B_{12}$ which was not described until 1948. Thus, all of the major vitamins were not described until the first half of this century although the properties of certain vitamins were known considerably earlier. The knowledge that fresh fruits (particularly citrus fruits) contain some factor that prevents scurvy goes back at least several hundred years. Apocryphally, the practice of the British Navy of providing limes to their sailors on long ship voyages to prevent scurvy is responsible for the common nickname of "limeys" given to British sailor.

It seems likely that all of the "vitamins" (meaning important food factors beyond fats, carbohydrates and proteins) have not yet been discovered. This is probably at least partially responsible for the current interest in "herbal medicine" and functional foods wherein ingestion of various natural products are supposed to have particular health benefits. The studies on heart disease over the last thirty years also make it clear that not only is it important to add vitamins and other factors to the diet, it is also important to avoid certain food substances that were formerly supposed to be benign. In particular the ingestion of saturated fats, generally of animal origin, has been shown to result in artery damage and an overall lessening of cardiac fitness.

It was with some surprise that the anti-fat crusaders discovered that certain Southern European diets that are exceptionally high in saturated fats do not produce the same degree of heart disease as do fatty diets in the United States. This finding led to a search for a "protective factor" to neutralize the baneful effects of dietary fats. Several candidates rapidly came to the forefront. The Mediterranean diets are not only high in saturated fats from meats and cheeses, they are also high in mono-unsaturated fats, particularly from olive oil. There are some studies that suggest that mono or poly-unsaturated fats can at least partially neutralize the harmful effects of saturated fats. At the same time the European diet also includes a significant amount of alcohol usually in the form of red wine. There is some evidence that moderate alcohol consumption has an ameliorating influence on the circulatory system.

More importantly, perhaps, tannins or polyphenols found in red wine are powerful antioxidants. There is growing evidence that dietary antioxidants prevent a number of maladies including heart disease. Antioxidant vitamins such as vitamin C and vitamin E are strongly implicated in the prevention of heart disease and a number of other diseases. Certainly, the dietary suggestion of at least five servings per day of fruits and vegetable provides abundant antioxidants in the form of antioxidant vitamins as well as antioxidant polyphenolic compounds.

Studies of human nutrition have shown that a shortage of dietary antioxidants results in "oxidative stress" in which uncontrolled free radical production results in oxidative damage to proteins, lipids and nucleic acids. Antioxidants provide a biochemical environment that does not favor production of free radicals. Further, any free radicals that are formed are rapidly neutralized by antioxidants. Therefore, it is not surprising that a number of techniques have been developed to measure the presence of antioxidants. It is desirable to measure the antioxidant capacity of various foods as a way of estimating potential benefit from various foods or food additives. It is also beneficial to measure antioxidant levels of blood, urine, and other medical samples to asses the antioxidant status of a given patient and to determine the effect of ingesting various antioxidants on that antioxidant status.

A number of different analytic tests are used to determine antioxidant and/or "free radical trapping" content of foods. To the extent that many important antioxidants are polyphenolic compounds test, such as bromine reduction tests, for polyphenols are employed. A series of other tests are used to determine free radical trapping. The total (peroxyl) radical-trapping antioxidant potential (TRAP) assay employs 2'-azobis-(2'amidinopropane)-dihydrochloride to initiate formation of peroxyl radicals in a test substance. An oxygen electrode is then used to measure the rate that a given lipid sample resists peroxidation (e.g., by measuring the rate of oxygen uptake) in the presence of various test antioxidants. This method is generally most effective at measuring lipid soluble antioxidants and does not give a straightforward antioxidant value.

The trolox-equivalent antioxidant capacity (TEAC) is another method that measures the ability of antioxidants to prevent or quench free radicals. 2,2'azinobis-(3-ethylbenzothiazoline-6-sulfonic acid) (ABTS) is reacted with hydrogen peroxide in the presence of a peroxidase enzyme to form radical cations whose presence can be detected optically by their effect on 6-hydroxy-2,5,7,8-tetramethylchroman-2-carboxylic acid (trolox). The method measures the inhibition of free radicals by antioxidants in the sample. This method requires several fairly complex reagents.

The oxygen radical absorbance capacity (ORAC) assay uses AAPH to generate peroxyl radicals. The radicals are optically measured as the fluorescence quenching and/or destruction of the algal pigment $\beta$-phycoerythrin. The assay can be automated allowing the free-radical quenching power of samples to be analyzed. Generally, instruments capable of fairly sophisticated optical measurements (e.g., fluorescence life time or total fluoresecence measurements) are required.

The total oxyradical scavaging species (TOSC) assay quantifies the reactive oxygen species scavaging potential of antioxidants. In this test ABAP is thermally decomposed to generate peroxy radicals which in turn generate ethylene gas by oxidatively decomposing $\alpha$-keto-$\gamma$-methiobutyric acid. Antioxidants that scavenge the reactive oxygen prevent or diminish the formation of ethylene which is measured by a gas chromatograph. Again fairly complex and sophisticated instrumentation is required. Other complex analytic equipment such as electron spin resonance (ESR) spectrometers can also be employed to measure scavenging of free radicals by antioxidants.

Antioxidants can be measured in plasma using the fairly simple FRAP oxidation-reduction assay which optically measures the reduction of ferric-tripyridyltriazine to a ferrous form. This test is somewhat simpler than the toxic bromine test mentioned above.

SUMMARY OF THE INVENTION

The present invention uses a simple redox reaction to measure the antioxidant level of foods and medical specimens such as urine. A stable, non-toxic complex of iodine is added to the material to be measured. Antioxidants in the sample to be measured reduce elemental iodine to iodide ion which is readily measured with a highly sensitive iodide electrode. The instrumentation involved is extremely simple since the iodide electrode is extremely rugged and can be used with pH meters and similar analytic instruments. Because portable meters are readily available, the test can be readily used in field work as well as laboratory analysis. Although the test is primarily intended to measure water soluble antioxidants, it can also measure fat soluble antioxidants albeit more slowly. This is a result of the hydrophobic properties of elemental iodine. If the iodine reagent is emulsified with an organic phase, the iodine will transfer into the organic phase and undergo reduction by any antioxidants present. If the emulsion is "broken" (e.g., through addition of a wetting or antifoaming agent) or mixed with an aqueous phase, the resulting iodide ions will transfer into the aqueous phase and may be measured therein. Another approach to measuring fat soluble antioxidants is to dissolve them in a water miscible organic liquid such as alcohol (methanol, ethanol, propanol or butanol), benzyl alcohol or glyme ethers, etc. The PVP-I reagent can be mixed with these solvents so that the iodine dissolves. After the reaction, the solvent is mixed with water to facilitate measurement of the iodide ions.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an iodine-based redox measurement of antioxidants.

As already mentioned, the present test is based on the reduction of elemental iodine by antioxidant compounds. In this process each iodine atom receives an electron and becomes an iodide ion. According to standard oxidation-reduction reactions the iodine will be reduced by any compound that has a standard oxidation reduction potential that is more negative than the +0.54 volt half cell potential of an iodine/iodide cell. This oxidation reduction range includes many important antioxidants including vitamin C and tannins.

In theory the reactive elemental iodine could be provided in a variety of different forms. However, iodine is relatively insoluble in aqueous solutions. The tri-iodide (e.g., iodine + iodide) is readily soluble but it is relatively corrosive and somewhat toxic (although not nearly as toxic as complex organic chemicals used in some antioxidant tests). Therefore, the present test can be carried out with ti-iodide solutions (Lugol's solution), but this is not the preferred method because of the higher iodide background and because of the potential toxicity of the reagent. Elemental iodine can be rendered water soluble and essentially non-toxic by any of a number of iodine coordinating materials which are also known as iodophors. The most popular iodophor is probably polyvinylpyrrolidone (povidone). An iodine-polyvinylpyrrolidone complex (povidone iodine or PVP-I) is commercially available. The method of the present invention employs a 10% aqueous solution of PVP-I. Because the PVP-I is about 10% by weight elemental iodine in the dry state, the 10% reagent solution provides 1% elemental iodine by weight. Of course, a range of PVP-I concentrations are useable and grades containing different percentage weights of iodine can also be used.

The method of the present invention is as simple as adding an aliquot of the PVP-I reagent to an antioxidant solution and measuring the conversion of iodine to iodide with an iodide electrode. Of course, the method depends on an excess of iodine so that all available antioxidant will be oxidized. This is readily achieved by measuring serial dilutions of the unknown substance. When the dilutions produce a linear result (e.g., a one to one dilution produces one half as much iodide ion), one is assured that the proper excess of iodine is being maintained. A simple way of assuring that adequate iodine is present to guarantee linearity is to observe the color or the reaction solution. The initial PVP-I solution has a fairly intense red/brown color. As the reaction proceeds, colorless iodide is formed so that the overall color fades. If the solution becomes entirely clear, then insufficient iodine was present to result in a correct measurement. The sample should be diluted and the experiment repeated. The visible lightening of the color of the solution is an indication that the sample contains a potent antioxidant. The method can be readily calibrated by measuring known amounts of a reducing agent such a vitamin C or sodium bisulfite.

A significant advantage of the method is the ability to carry out the test almost anywhere with simple reagents and compact equipment. The preferred method for measuring iodide concentration is a portable ion selective electrode (ISE) and meter such as those manufactured by Orion Instruments, Inc. After calibration of the electrode by establishing a calibration curve through the use of a known concentration of antioxidant (reducing agent), the experimental substance can be measured. As already explained, the method works by measuring the formation of iodide ions as the sample antioxidant reduces iodine in the PVP-I reagent. However, the sample may contain iodide to begin with, and the PVP-I reagent does contain iodide in the absence of any antioxidant. These additional sources of iodide must be corrected for. The experimental results are expressed as Iodine Reducing Units (IRU/volume) wherein the IRU value represents final iodide concentration at completion of the reaction (in parts per million). The IRU value is corrected by subtracting any iodide reading in the sample prior to the addition of the PVP-I reagent and by subtracting the iodide reading of the PVP-I reagent without addition of any antioxidant sample. Since iodide reduction is directly related to antioxidant capacity, IRUs can legitimately be called "Anti-Oxidant units" or AO units. A material with twice the antioxidant capacity of another material will show an IRU reading that is twice as great.

EXAMPLE 1

Effect of Dietary Antioxidants on Urine

This experiment was undertaken to determine the effect, if any, on the ingestion of dietary antioxidants on the antioxidant status of urine. In other words, if antioxidant materials are eaten, is there a significant excretion of antioxidants? For this experiment a highly concentrated polyphenolic antioxidant prepared from cranberries was used (trade named SHANSTAR™). The subject ingested a three gram sample of the cranberry antioxidant. A reference urine sample was taken a time zero and at 30 min intervals for the first two hours and then hourly until six hours had elapsed.

For each measurement a 25 ml aliquot of urine was placed in a 50 ml tube and any background iodide present was determined. Then 2.5 ml of 10% PVP-I was added and the solution mixed thoroughly. The rise in iodide concentration was measured over a period of 30 min. Earlier experiments had determined that the reaction reaches completion within 30 min under these conditions. Finally, the effective iodide concentration of the PVP-I reagent was determined by adding 2.5 ml of PVP-I reagent to 25 ml of deionized water. The corrected (measured value minus initial iodide reading and minus reagent iodide reading) IRU values are shown in Table 1, below.

TABLE 1

| Time | Corrected IRU/ml |
|---|---|
| 0 min | 796 |
| 30 min | 1416 |
| 60 min | 1666 |
| 90 min | 1766 |
| 2 hr | 1316 |
| 3 hr | 786 |
| 4 hr | 666 |
| 5 hr | 566 |
| 6 hr* | 4116 |

*The 6 hr measurement was taken following ingestion of vegetable soup for lunch.

These results demonstrate an unusually rapid effect of increase in urinary antioxidant level following ingestion of antioxidants. It appears that excretion starts within 30 min of ingestion. Considering the rapidity with which the antioxidant impacts the urine it seems likely that absorption is directly into the blood stream through the buccal, esophageal or even stomach mucosa. It would also appear that peak secretion occurs within one and one half hours of ingestion and that values have returned to their base level within about 3 hr. Interestingly, the overall antioxidant level appears to decrease between meals thereby suggesting a possible value to between meal ingestion of antioxidant snacks. Clearly, vegetable soup is an excellent source of urinary antioxidant. It was noted that peak antioxidant levels coincided with a darkening (yellowing) of the urine color.

EXAMPLE 2

Additional Measurements of Dietary Antioxidants on Urine

The measurements of urine were repeated after determining the background antioxidant level of the subject's urine. Urine was measured as explained under Experiment 1. Over a four day period the IRU was determined at the same time each day. The reading varied between 200 and 220 IRU. Measurement showed that the urine always had a pH of 6.0. The subject then ingested 500 mg of concentrated cranberry antioxidant. The results are shown in Table 2.

TABLE 2

| Time | pH | Corrected IRU/ml |
|---|---|---|
| ingestion | 6.0 | 200 |
| 1 hr 45 min | 6.0 | 920 |
| 3 hr 15 min | 5.5 | 1220 |
| 4 hr 15 min | 5.5 | 1300 |
| 7 hr 15 min | 5.5 | 1320 |
| 17 hr 15 min | 5.5 | 1330 |

TABLE 2-continued

| Time | pH | Corrected IRU/ml |
|---|---|---|
| 19 hr 15 min | 5.5 | 1300 |
| 24 hr 45 min | 6.0 | 1120 |
| 28 hr 15 min | 6.0 | 900 |

This experiment covered a much greater period of time than the initial experiment. In addition, a much smaller dose of the antioxidant was taken as a capsule which would mitigate against buccal or esophageal absorption. It is likely that this form of administration slowed absorption of the material. Further, the composition was formulated with cellulose which might prolong the release of the material. The subject did not fast over the experimental period so that some of the readings may be influenced by other antioxidants from ingested food.

EXAMPLE 3

Antioxidant Level of Fruit Juices

For this experiment a number of different fruit juices were measured. Of course, commercial juices contain various concentrations of actual juice. Since these numbers were not normalized against "100%" juice, they are not truly comparable with each other. The juices had an initial iodide value of essentially zero. Therefore, the only correction needed was that for the iodide reading of the PVP-I reagent. As an indication of reaction rates, Table 3 shows corrected meter readings at 1, 5, 15 and 30 min. After 30 min there was little further change in iodide concentration.

TABLE 3

| Juice | 1 min | 5 min | 15 min | 30 min |
|---|---|---|---|---|
| white grape | 97 | 375 | 501 | 535 |
| apple | 466 | 756 | 826 | 1056 |
| blackberry[1] | 481 | 846 | 1236 | 1496 |
| blueberry[1] | 339 | 703 | 856 | 936 |
| raspberry | 1216 | 1786 | 2426 | 2376 |
| cranberry | 263 | 475 | 746 | 836 |

Sample was diluted 1:10 before measurement.

These results show that of these commercially available juices both blackberry and blueberry had by far the highest level of antioxidant (reducing agent). Note that the reaction slopes of the different juices varies considerably. Raspberry shows a relatively shallow slope due to a high IRU reading at one minute. Experiment has shown that simple soluble antioxidants such as vitamin C react very rapidly with the PVP-I reagent while complex tannins react more slowly. This would suggest that the raspberry juice has a very high level of vitamin C or a similar factor.

EXAMPLE 4

Antioxidant Level of other Plant-Based Food Products

Twenty five ml aliquots of commercial carrot juice and red wine ("burgundy") were measured as shown above. In addition, measurements were made of dried figs. One gram of finely chopped dried fig (chopped with a food processor) was suspended in 25 ml of water and incubated at room temperature for 60 min. Then the resulting solution was measured using the method of the current invention. The results are shown in Table 4

TABLE 4

| Food | Corrected IRU/ml |
| --- | --- |
| red wine | 110 |
| carrot juice | 70 |
| dried fig | 1430 |

As might be expected, the red wine contains a reasonably high level of antioxidants. The dried figs contains a surprisingly large amount of antioxidant. This comparison is somewhat hard to make because ideally the weight of solutes in each tested material would be known. It is possible that on a weight of solute basis the red wine contain the greatest amount of antioxidant.

EXAMPLE 5
Antioxidant Level of Eggs

Recently some egg producers have supplemented the feed of their laying hens with vitamin E to produce eggs that supposedly have enhanced antioxidant products. For this experiment "enhanced" eggs and regular eggs were measured using the method of the present invention. Four different egg samples were measured: a) liquid pasteurized eggs from vitamin E fed chickens; b) brand 1 of whole eggs from vitamin E fed chickens; c) brand 2 of whole eggs from vitamin E fed chickens; and d) whole eggs from chickens fed ordinary feed (control eggs). To measure the whole eggs two eggs were broken and the white and yolk homogenized. Twenty five ml of homogenized egg was diluted 1:2 with water and 25 ml of the resulting solution was tested as above. For the liquid eggs 25 ml was diluted 1:2 with water and 25 ml was measured as above. The results are shown in Table 5

TABLE 5

| Egg Sample | Corrected IRU/ml |
| --- | --- |
| a | 2190 |
| b | 2675 |
| c | 2645 |
| d | 932 |

These results confirm that vitamin E supplementation of chicken feed does result in eggs with significantly higher levels of antioxidant.

EXAMPLE 6
Antioxidant Level of "Health Supplements"

A variety of herbal supplements are currently touted as being especially rich in antioxidant properties. A number of herbal preparations were obtained and measured by the current method. One half gram of each supplement was suspended in 100 ml of deionized water (final concentration of 5 mg/ml assuming the supplements were fully water soluble). The corrected IRU values are given in Table 6, below.

TABLE 6

| Herbal Preparation | Corrected IRU/ml |
| --- | --- |
| green tea | 520 |
| saw palmetto | 29 |

TABLE 6-continued

| Herbal Preparation | Corrected IRU/ml |
| --- | --- |
| kava kava | −14 |
| Gingko biloba | 480 |
| korean ginseng | 18 |

These results show that the two materials widely believed to be especially high in antioxidants (green tea and Gingko) do, in fact, test high with the current method. The negative value of kava kava suggests that this material has little antioxidant detectable by the current method. Therefore, "instrument noise" may result in a negative value when subtractive corrections are made. Similarly, the values for saw palmetto and ginseng are so low as to be suspect.

The preferred way of practicing the current method is to measure iodide ion particularly with an ion sensitive electrode. Chemical methods of measuring iodide could also be used but would not be a convenient (or probably as accurate) as the ion electrode. Similarly, the method could be practiced by measuring the decrease in iodine as opposed to the increase in iodide. Again quantitative chemical methods could be employed but this would generally complicate the method and detract from its usefulness. Iodine can also be detected colorimetrically (e.g., spectrophotometrically) by extracting it into organic solvent. In this mode a rough concentration estimate can be made by comparing the resulting purple color to a standard card. While not as accurate as an iodide electrode such an approach does allow the current method to be practiced with minimal equipment.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the justdescribed preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method for determining relative amounts of simple soluble dietary antioxidants versus complex tannins in an aqueous liquid sample at room temperature comprising the steps of:

providing an aqueous liquid sample containing dietary material or a biological fluid to be tested;

contacting the sample with an aqueous solution of elemental iodine and polyvinylpyrrolidone at room temperature to form a mixture;

measuring a concentration of iodide ions at room temperature in the mixture at a plurality of time points over a time period after the contacting step by means of an iodide selective electrode; and measuring a slope of increase of the iodine ions over a time period from a first time Doint of about one minute from the contacting step to a later time point, wherein a shallow slope is indicative of simple soluble dietary antioxidants and a steep slope is indicative of complex tannins in said sample.

2. The method according to claim 1, wherein said liquid sample is a dietary material.

3. The method according to claim 1, wherein said liquid sample is a biological fluid.

4. The method according to claim 3, wherein the biological fluid is urine.

5. The method according to claim 1, wherein the later time point ranges from about 5 minutes to about 30 minutes.

6. The method according to claim 1, wherein the concentration of iodide ions at the first time point is indicative of simple soluble dietary antioxidants.

* * * * *